United States Patent
Willi et al.

(10) Patent No.: US 7,642,521 B2
(45) Date of Patent: Jan. 5, 2010

(54) LASER IRRADIATED HOLLOW CYLINDER SERVING AS A LENS FOR ION BEAMS

(75) Inventors: Oswald Willi, Duesseldorf (DE); Julien Fuchs, Paris (FR); Marco Borghesi, North Ireland (GB); Toma Toncian, Duesseldorf (DE)

(73) Assignees: Heinrich-Heine Universitaet Duesseldorf, Duesseldorf (FR); Université Pierre and Marie Curie (UPMC), Paris (FR); The Queen's University of Belfast, Belfast (GB); The Centre National de la Recherche Scientifique, Paris (FR); Ecole Polytechnique, Palaiseaux (FR)

( * ) Notice: Subject to any disclaimer, the term of this patent is extended or adjusted under 35 U.S.C. 154(b) by 92 days.

(21) Appl. No.: 11/908,698

(22) PCT Filed: Mar. 10, 2006

(86) PCT No.: PCT/EP2006/002249

§ 371 (c)(1),
(2), (4) Date: Apr. 8, 2008

(87) PCT Pub. No.: WO2006/097252

PCT Pub. Date: Sep. 21, 2006

(65) Prior Publication Data

US 2008/0191143 A1 Aug. 14, 2008

(30) Foreign Application Priority Data

Mar. 16, 2005 (DE) ........................ 10 2005 012 059

(51) Int. Cl.
*H01J 1/50* (2006.01)

(52) U.S. Cl. ................................ 250/396 R; 250/492.2; 250/398; 250/426; 250/423 R; 250/423 P; 250/424; 250/396 ML; 250/492.3

(58) Field of Classification Search .......... 250/396 ML, 250/492.2, 398, 426, 423 R, 423 P, 424, 396 R, 250/492.3
See application file for complete search history.

(56) References Cited

U.S. PATENT DOCUMENTS

| 5,382,866 | A | 1/1995 | Boggasch et al. |
| 6,852,985 | B2 * | 2/2005 | Cowan et al. ............ 250/423 P |
| 6,998,353 | B2 | 2/2006 | Erokhin et al. |

FOREIGN PATENT DOCUMENTS

EP    0225717 A1    6/1987

OTHER PUBLICATIONS

Gabor D, "A space-charge lens for the focusing of ion beams", Nature, Bd.160, Nr. 4055, Jul. 19, 1947, Seiten 89-90, XP009068124.

(Continued)

*Primary Examiner*—Bernard E Souw
*Assistant Examiner*—Meenakshi S Sahu
(74) *Attorney, Agent, or Firm*—Millen, White, Zelano, Branigan

(57) ABSTRACT

The present invention concerns a system for the focusing and/or a collimation of an ion beam, in particular a beam of accelerated protons, wherein the system has a lens with a lens body that is permeable to the ion beam, wherein means for the generation of an in particular electrostatic field, propagating within the lens body and focusing the ion beam, are provided, wherein the lens body has a wall of low thickness, wherein the means for the field generation comprise a source of electromagnetic radiation, whose emitted beam is directed onto the outer side of the wall of the lens body, wherein the thickness of the wall and the quality of the electromagnetic radiation is chosen such that the radiation generates free electrons that emerge from the wall and accumulate on the exit side of the wall in an electron cloud.

18 Claims, 5 Drawing Sheets

OTHER PUBLICATIONS

Govil R et al, "UV laser ionization and electron beam diagnostics for plasma lenses", Particle Accelerator Conference 1995, Proceedings of the 1995 Dallas, TX USA, May 1, 1995 New York, NY USA, Bd.2, Seiten 776-778, XP010165774.

Mackinnon A J et al, "Proton radiography as an electromagnetic field and density perturbation diagnostic", Review of Scientific Instruments, Bd.75, Nr.10, Oct. 2004, Seiten 3531-3536, XP002387021.

Roth M et al, "Energetic ions generated by laser pulses: A detailed study on target properties", Physical Review Special Topics-Accelerators and Beams, Bd.5, Jun. 4, 2002, Seiten 061301-1-061301-8, XP002387022.

Toncian T et al, "Ultrafast Laser-Driven Microlens to Focus and Energy-Select Mega-Electron Volt Protons" Science, Bd.312, Nr.5772, Apr. 21, 2006, Seiten 410-413, XP002387023.

* cited by examiner

LASER IRRADIATED HOLLOW CYLINDER SERVING AS A LENS FOR ION BEAMS

The present invention concerns a system for the focusing and/or for the collimation of an ion beam, in particular a beam of high energy protons, wherein the system firstly has a lens with a lens body suitable for the passage of the ion beam, wherein moreover means are provided for the generation of an in particular electrostatic field, wherein the field spreads out within the lens body and focuses and/or collimates the ion beam. The invention furthermore concerns a method for the focusing and/or collimation of the ion beam.

It is of known art to focus high-energy ion beams with, for example, electrical or magnetic quadrupole lenses. Since quadrupoles only focus in one plane, whereas they defocus in the other plane, they are usually arranged in a multiplet one behind another in the beam path. Here the focusing effect of the quadrupole lenses is limited by the field that can be generated at the pole shoe. In addition to quadrupole lenses there are other electrical and magnetic lenses with rotational symmetry that are also of known art. All systems of known art are relatively complex in construction and are not very suitable for ion beams with a large energy bandwidth, as is the case for laser-induced proton beams. Here these laser-induced proton beams are generated by irradiation of a thin foil with ultra-short (fs-range) and high-intensity (~$10^{19}$ watts) laser pulses.

From the prior art moreover Gabor (plasma) lenses are of known art, which with reference to their optical properties can be compared with wire lenses, wherein high-energy ion beams are focused by means of an azimuthal magnetic field, which is elicited by an axial current generated by a plasma discharge. This plasma discharge is generated with electrodes that are arranged within the lens body. Plasma lenses are extremely complex and therefore find application almost exclusively in research devices in heavy-ion physics and high-energy physics. Plasma lenses are not very suitable for practical use in medical therapy equipment, for example.

The object of the invention is now to create a system that is convenient to manipulate, can be implemented in a cost-effective manner with simple means, and has outstanding focusing and/or collimating properties for high-energy ion beams that also have a large energy bandwidth. The object is moreover to create a simple method for the focusing and/or collimation of high-energy ion beams.

This object is achieved by means of the system according to claim 1 and the method according to claim 10. Particularly advantageous forms of embodiment are cited in the respective dependent claims.

The basic concept of the invention lies in forming an in particular electrostatic field within the lens body by means of external impingement of the lens body with electromagnetic radiation, the field line characteristics having a collimating and/or focusing effect on the ion beam passing through the lens body. Here a comment should be made at this point that the formation of such a field within a hollow lens body advantageously consisting of conducting material is possible under certain circumstances, even if this phenomenon contradicts the rule of physics, familiar from the Faraday cage, concerning the complete loss of field in the interior of a conducting body. This effect is observed in principle, if to a much lesser extent, with the irradiation of insulating material.

The formation of the field within the lens body is based on the above-cited effect, which is also responsible for the laser-induced proton beams. Here an essentially electrostatic nature is to be ascribed to the field. Thus the interaction of intensive laser pulses with a thin foil, in particular of conducting metal, generates electron beams and proton beams with high energy and density in and/or on the surface of the foil. These plasma electrons are accelerated at right angles to the foil surface, as a result of which strong spatial charges form, since the protons, many times heavier, cannot follow. High field strengths of up to $10^{12}$ V/m thus appear on the rear face of the foil. In the case of a hollow body manufactured from such a foil this means that electron clouds form on its inner wall and the charge moves over the inner surface, as a result of which a field is formed within the cylinder that in this case is radially directed.

This electrical field has a corresponding effect on the ion beam passing through the cylinder, which in the case of the radial field is a focussing or collimating effect. The fact that targets irradiated with high intensity laser pulses experience a short duration accumulation of positive charge, on account of the generation of laser-driven hot electrons, is confirmed by experiments. An estimate on the basis of experimental data shows that a charge Q of approximately $2.5 \cdot 10^{-8}$ C and an electrical field of approximately $10^{10}$ V/m can occur. The electrical field linked with such an accumulation of charge is able by itself to deflect protons with an energy of several MeV.

To what extent this effect forms depends on the thickness of the wall and the quality, in particular the energy density, of the electromagnetic radiation. These parameters must be adjusted such that the beam, as described above, generates free electrons in the wall that have sufficient energy to penetrate through the wall and to form an electron cloud on the inner side of the wall. For this effect the geometry of the lens body does not play any significant role in the first instance. Thus the lens body also does not necessarily need to have a closed jacket surface. However care must be taken that the possibility of a homogeneous charge distribution in the wall is provided. One should therefore be dealing with a surface that is more or less closed. Since the configuration of the lens body has an influence on the shape of the field, an axisymmetric shape is to be preferred.

In order to achieve the effect to be exploited according to the invention, this requires, as stated, on the one hand a lens body with a thin wall, where in the case of laser intensities of approximately $10^{19}$ W/cm$^2$ wall thicknesses of between approximately 0.01 mm and 0.1 mm are considered to be thin-walled. Here the possible limiting thickness of the wall is defined via the quality of the electromagnetic radiation, which must generate the described effect within the material. The desired effect can be achieved with laser pulses of an intensity of approximately $10^{19}$ W/cm$^2$ impacting on a Ni foil approximately 50 μm thick.

For maintenance of a particularly good focussing effect it is advantageous if a hollow cylinder with a circular cross-section is used as a lens body, wherein the outer wall is irradiated with a high intensity short pulse laser, generating a temporary accumulation of charge. Within such a hollow cylinder a radial field forms. A focussing effect is e.g. observed, if the cylinder that is laterally irradiated by the laser has a diameter of approximately 1 mm. As a result of the irradiation a transient accumulation of positive charge occurs on the cylinder, and thus the electrical field is created, whose field lines stand at right angles to the cylinder surface. By means of this electric field the ions, in particular high-energy protons, are deflected in the direction of the cylinder axis, and are thus focussed.

In general the kind of focussing according to the invention can be applied to any ion beams from any sources, where in general the ions can also experience an acceleration. In an advantageous form of embodiment, however, the system according to the invention is additionally equipped with an ion source, which generates accelerated ions without a separate acceleration section and without further structural complexities. As a source for protons laser-induced proton beams again lend themselves, since an appropriate laser beam, as described above, is already available. With such an ion source it is possible to conceive a compact system that is convenient to manipulate and is suitable for use in medical therapy. Even if it is possible to use two separate, but synchronised, lasers, it is however advantageous to provide means in the system that divide the beam of a single pulsed laser.

Here the protons are generated using one part of the beam and the lens is charged with the other part of the beam. In order to be able to undertake an energy selection of the protons it is advantageous to provide an, in particular variable, retardation of the beam component impacting the lens relative to the beam component generating the protons. With the system according to the invention in addition to the focussing and collimation the energy selection is also possible, so that the proton beam can be adapted for a multiplicity of applications. In this manner the invention forms an important and flexible intermediate tool in order to be able to bring the proton beam into a suitable shape for a particular application. Here the selective focussing of particular energies depends on the life of the electrostatic field, which after a certain time collapses either as a result of charges flowing away, or by the recombination of charge carriers. Here the velocity with which the charge can flow away is a function of the mode of suspension of the lens body. Thus with a suspension that is electrically insulated as well as possible, for example, using very thin wires and a vacuum, the fields persist within the lens body for approximately 100 ps. Here the following applies: the faster the discharge occurs, the more selectively the lens focuses a particular energy.

In general alongside medicine, in particular tumour therapy, there are a wide variety of applications for proton and ion acceleration using ultra-short intensive laser pulses. The following can be named, for example: inertial fusion energy, isochore heating of materials, proton lithography, proton radiography, the investigation of internal structures of static or dynamic systems, and also the detection of electrical and/or magnetic fields that are formed during the interaction between intensive laser pulses and high density material.

As already described, the high energy protons arise in the interaction between the high intensity laser pulse and the dense material, with power densities of more than $10^{19}$ W/cm$^2$ being achieved. Here the protons emerge in a collimated beam from the rear face of the foil with several MeV of energy and relatively little divergence. The acceleration has taken place within the laser-irradiated thin foil. Protons beams occur even if the target nominally does not contain any hydrogen. The proton beam has unique properties, namely a small source size, little divergence, short duration and a high density of up to $10^{12}$ protons with several MeV of energy. In comparison to conventional sources such a source is thus particularly advantageous. However, the proton beams thus generated cover a large energy bandwidth.

Here theoretical models advise that the protons draw their energy from the enormous electrical field of up to one MeV per micron, which is formed by the laser-accelerated, fast electrons via the spatial charge on the rear target surface. From simulations it arises that the charge of the proton beam is neutralised by an accompanying cloud of electrons. According to the models the protons are accelerated in accordance with the laser pulse duration of less than 1 ps. It therefore appears not possible to focus such a laser-induced proton beam with means other than the system according to the invention.

A further advantage of the system according to the invention is the relatively high repetition rate with which the focussed proton pulses can regenerate. This depends simply on the potential of the laser used, with repetition rates of 10 Hz already possible at the present time according to power. Thus the system becomes of even more interest, for medical applications in particular.

In what follows the invention is elucidated in more detail with the aid of FIGS. 1 to 5. In the figures.

Figure 1:
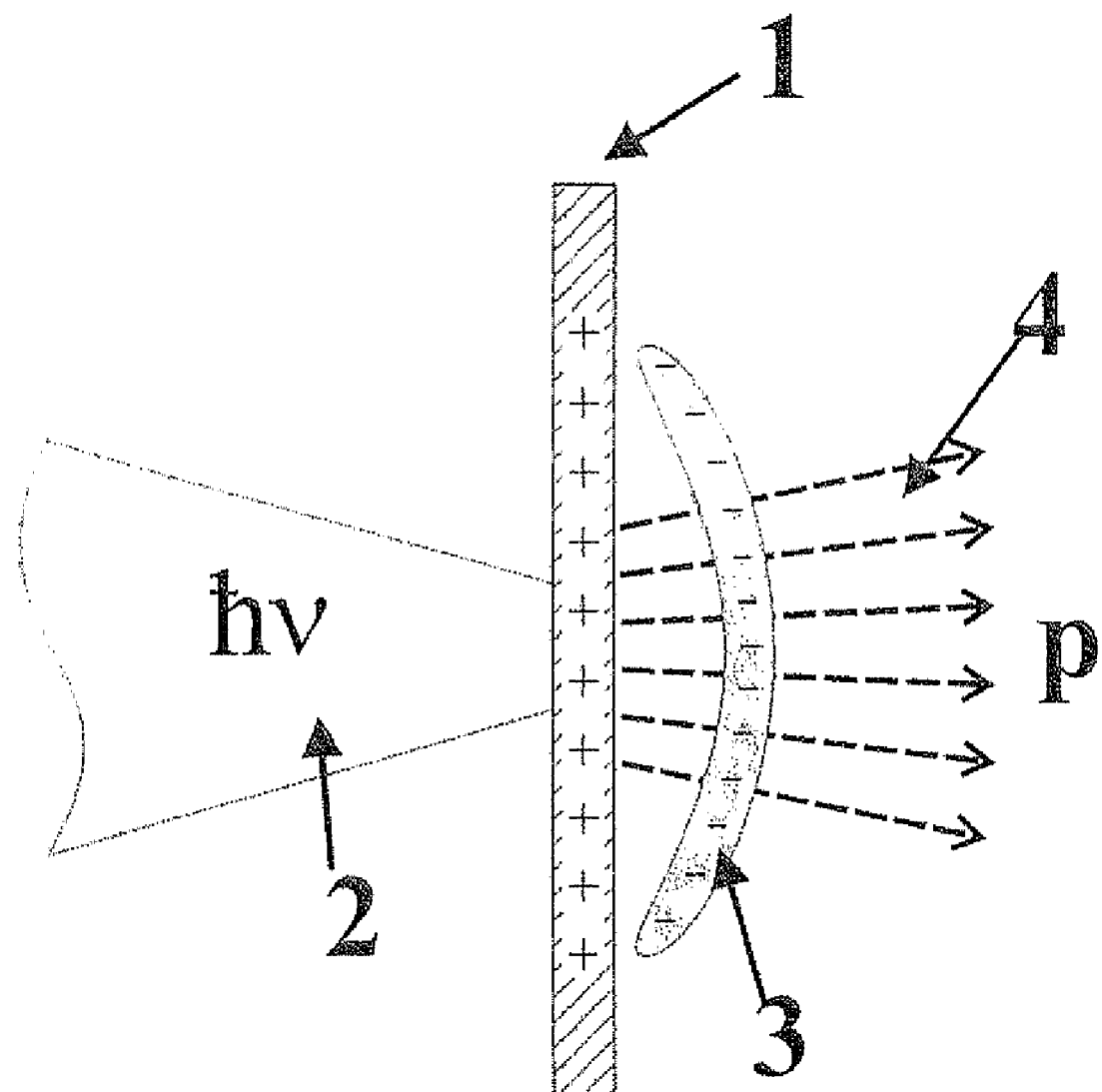
FIG. 1 shows the scheme for the generation of a laser-induced proton beam.

FIG. 1 shows an approximately 50 µm thick Al-foil 1, onto which a short laser pulse 2 has impinged. With an appropriate laser power the electrons in the foil 1 are entrained and emerge on the rear face of the foil 1. There they form a negatively charged electron cloud 3, with a positive charge accordingly remaining in the foil.

Figure 2:
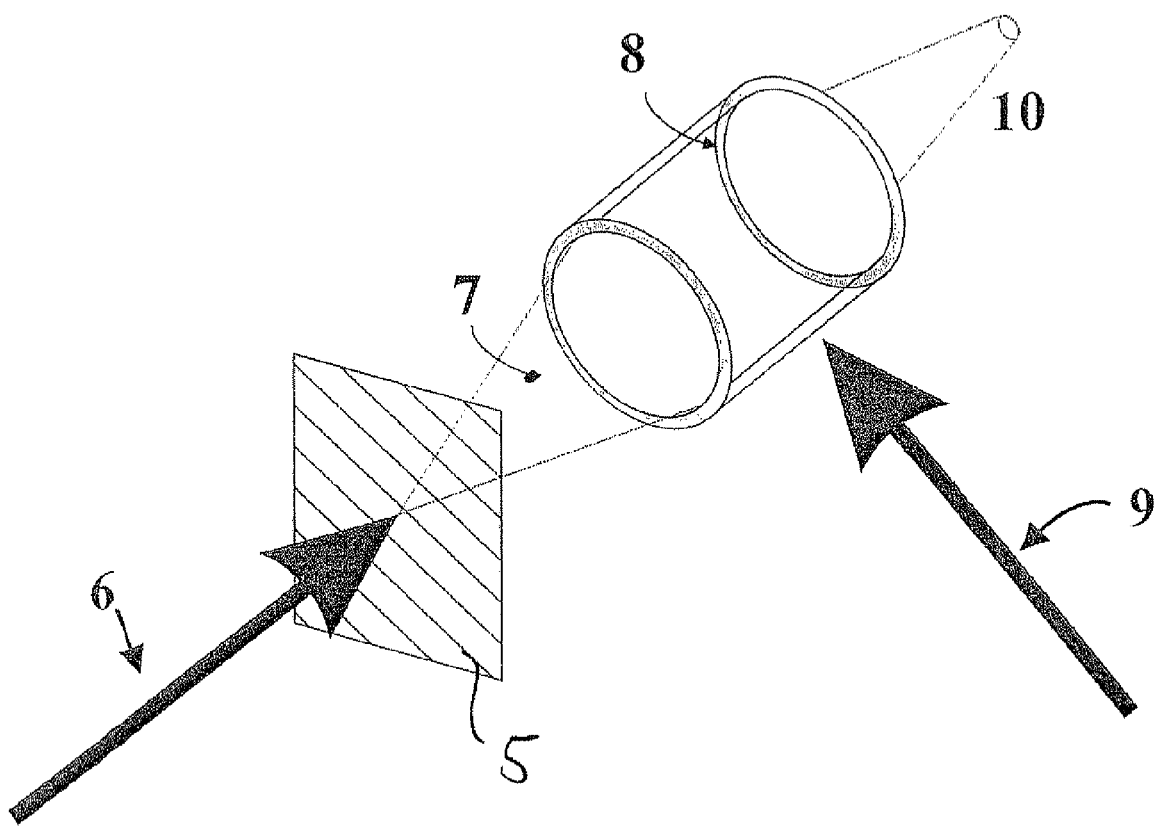
FIG. 2 shows a lens in the beam path of the proton beams

This spatial charge, present for the duration of the pulse, accelerates remaining protons (p) in the foil, the protons emerging as a beam 4 on the rear face of the foil, FIG. 2 shows a system according to the invention for the focussing of a proton beam generated by means of a laser. With an arrangement as described in FIG. 1, a proton beam is generated with a divergence of between 10° and 20° by means of a laser pulse 6 directed onto a thin foil 5 with a power of approximately $10^{19}$ W/cm$^2$ and a pulse duration between approximately 40 fs and several picoseconds. As a central element the system has a lens with a lens body permeable to the proton beam in the shape of a hollow cylinder 7 that is formed from aluminium of a thickness between 25 µm and 50 µm. The hollow cylinder 7 has a length of approximately 1 mm to 3 mm and a diameter of between 0.5 mm and 1.3 mm.

As a means for the generation of an electrical field within the hollow cylinder a further laser beam 9 is provided, which is directed onto the outer side of the wall of the hollow cylinder 8. In this case the laser beam 9 and the laser pulse 6 originate from the same source, and therefore have the same pulse characteristics. One is dealing with a time-delayed partial beam of the same laser, not represented. The electrical field generated in the hollow cylinder 8 by the laser pulse 9 focuses the divergent proton beam 7 into the proton beam 10. The incoming proton beam 7 experiences the focusing effect and leaves the cylinder as a collimated partial beam 10 with a cross-section that is smaller than the cylinder radius. The proton flow measured behind the hollow cylinder 8 is higher by a factor of three to nine than in the unfocused case, which shows that all the protons entering the cylinder are focused.

Since the electrical field generated in the cylinder is only of short duration, corresponding to the pulse duration of the laser beam 6, only those protons are collimated that are passing through the hollow cylinder 6 while it is being charged. Since these protons required a certain time for the passage between the foil and the hollow cylinder 8 the system selectively collimates the protons of a certain energy from the broad energy spectrum of the original proton beam. Moreover it is advantageous if a mask is arranged at the outlet that only allows the passage of the collimated part of the beam. Thus it is possible individually to tailor the energy of the incident proton beam to the application in question, e.g. proton therapy for cancer treatment.

Figure 3:
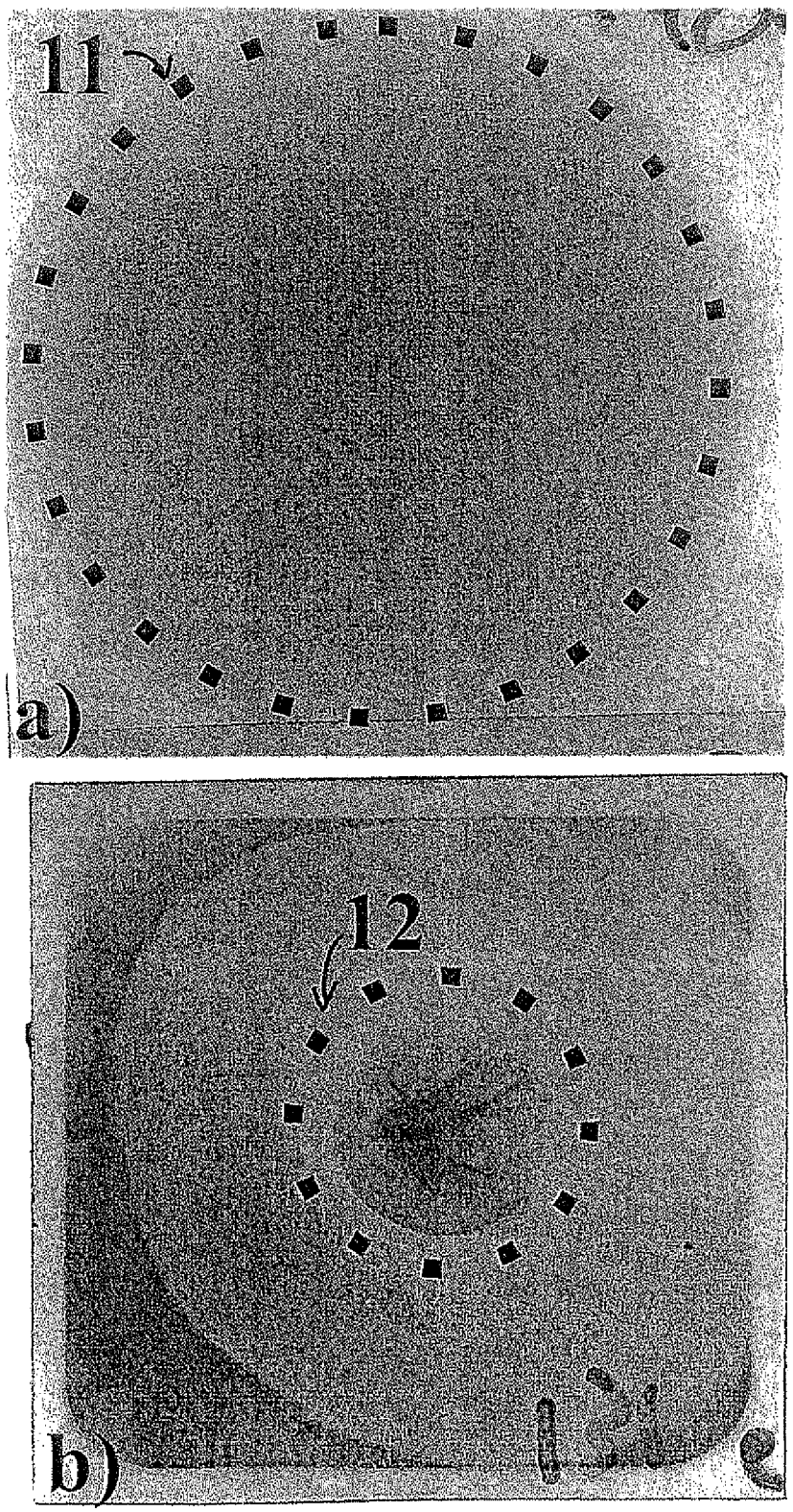
FIG. 3 shows divergences of proton beams investigated.

FIG. 3 represents the focusing effect of a hollow cylinder on which laser pulses have impinged with the aid of two images. For this purpose a radiochromic film was introduced into the beam path and was impinged by the beam. Such a film alters its level of blackness to a greater or lesser extent according to the irradiation. FIG. 3a shows the profile of the unfocused proton beam with a large divergence 11. In this case the film is approximately distant 2 mm from the foil 5 and therefore from the proton source. In contrast the proton beam in 3b, as described above, has been focused by means of a hollow cylinder and has a correspondingly small divergence 12, which can clearly be detected in the significantly reduced size of the beam spot.

Figure 4:
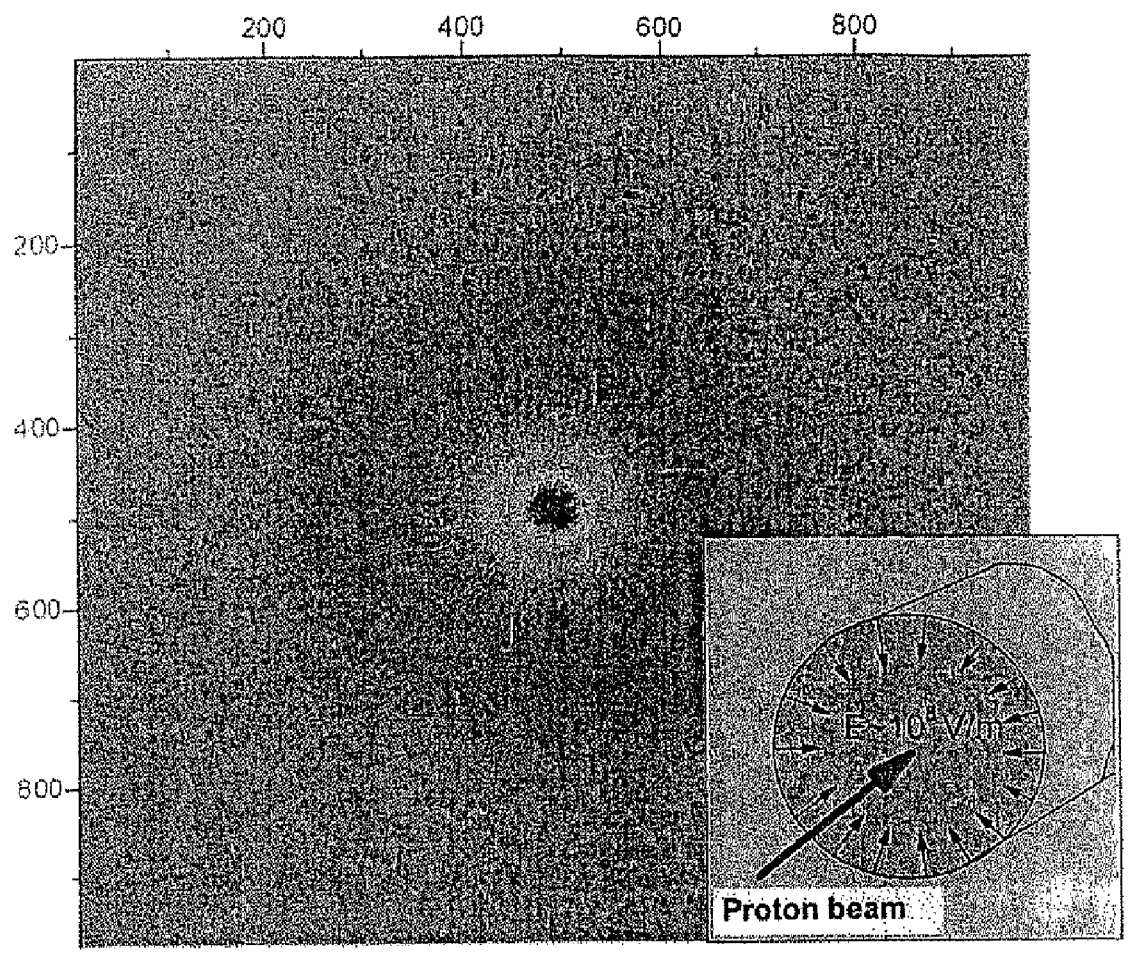
FIG. 4 shows the result of a simulation.

Here the film is arranged approximately 3.5 mm distant from the foil 5. The focusing effect can be reconstructed in a simulation of the individual particle tracks (FIG. 4). Here a radial electrical field of $10^8$ V/m has been assumed within the cylinder. With the aid of the grey levels the simulation shows an increase of intensity in the centre of the proton beam leaving the hollow cylinder that has been charged by the laser pulse. The dimensions on the axes of the figure represent the beam width in microns. The insert in FIG. 4 shows the assumed distribution of the electrical field within the cylinder. As a result the protons are deflected within the cylinder in the direction of the cylinder axis. Depending on the length of the cylinder this leads to a collimation of the proton beam on the axis, which can be observed in the experiment, as shown in FIG. 5.

Figure 5:
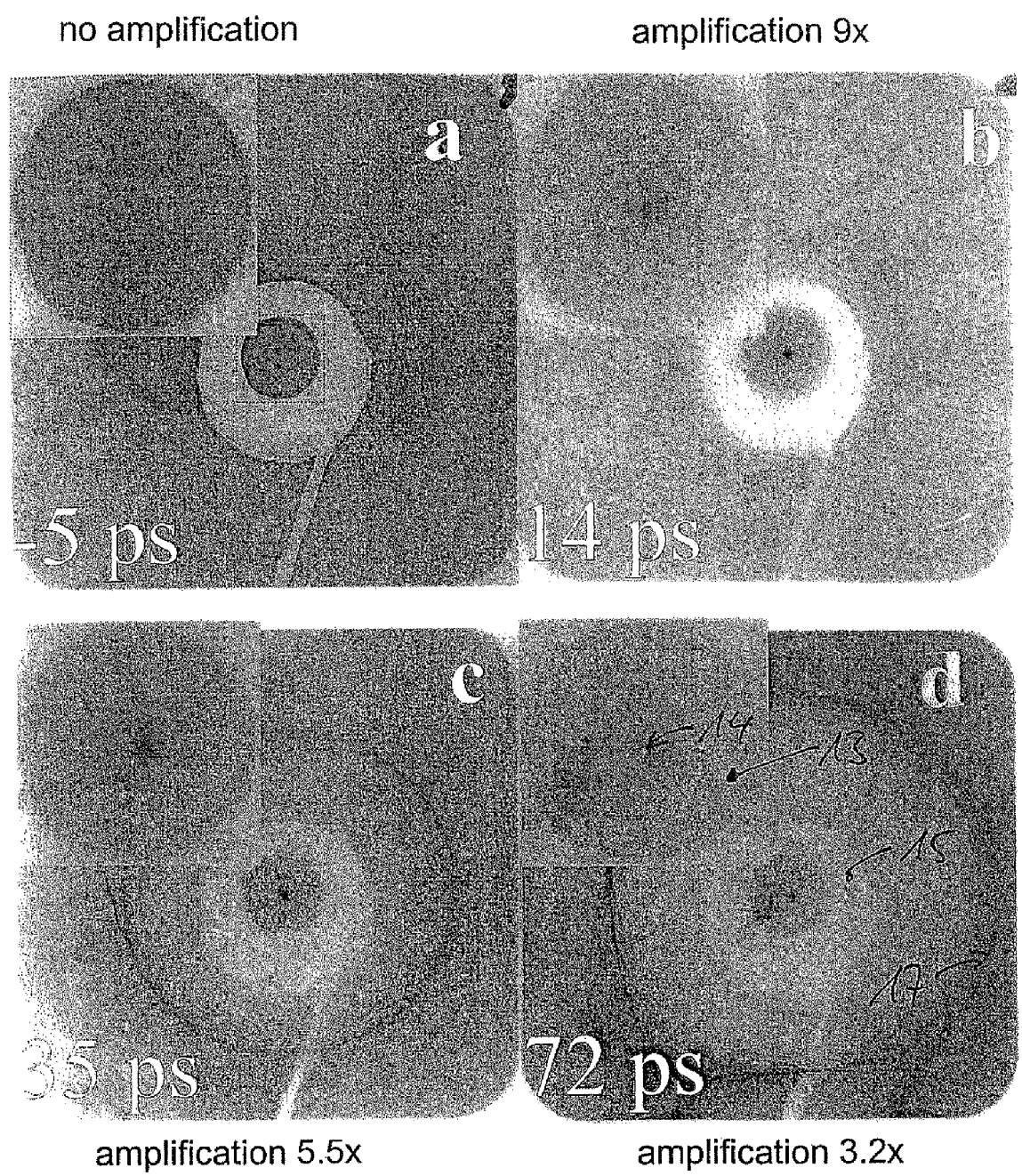
FIG. 5 shows the result of a measurement.

Here the following test rig was put together for the measurements according to FIG. 5: The cylinder had an internal diameter of 650 μm and a wall thickness of 50 μm. It was made of Dural (94% Al, 4% Cu, 1% Mg). It had a length of 3 mm. The entry opening of the cylinder was 5 mm distant from the foil 5.

In order to investigate the collimated proton beam a stack of a plurality of radiochromic films was arranged at a distance of approximately 4 cm behind the hollow cylinder, onto which the collimated proton beam was directed. The grey levels make clear the intensity of the irradiation, for which it is true that: the higher the intensity, the blacker the colouring. The foils a) to d) were ordered starting from the rear, where a) was the rearmost foil of the stack. The details show in each case the interior of the cylinder. In the case of a) it can be detected that no focusing of the particularly high energy protons has taken place, since the pulse generating the field in the lens body only impinged on the latter 5 ps after the passage of these protons through the lens body. In this respect it is also not possible to detect any focusing effect in the form of an amplification. The protons leave behind a colouration on the foil b); these protons passed through the cylinder 14 ps after the impingement of the laser pulse generating the field. The focusing effect can clearly be detected; this accounts for an amplification by a factor nine relative to the unfocused beam. An amplification of 5.5 can be detected in the case of the protons impinging after 35 ps (foil c), while in the case of the protons with lower energy that impinged after 72 ps onto the first foil d) the effect has already decreased and is accompanied by a factor of only 3.2. On the foil d) the edge 13 of the hollow cylinder with the central focus 14 can clearly be detected. The region 15 of lower intensity is caused by the shadow of the hollow cylinder. This is bounded by a region 16 that was subjected to a further proton flow that has passed by the hollow cylinder. As a result of the charging up of the cylinder wall an accumulative effect occurs outside the hollow cylinder that is represented by the ring 17.

The invention claimed is:

1. A system for the focusing and/or for the collimation of an ion beam, comprising a lens with a lens body permeable to the ion beam, wherein means are provided for the generation of an electrostatic field extending within the lens body and focusing the ion beam, and wherein the lens body has a wall of low thickness, wherein the means for the field generation comprises a source for electromagnetic radiation, whose emitted beam is directed onto the outer side of the wall of the lens body, wherein the thickness of the wall and the quality of the electromagnetic radiation is chosen such that the radiation generates free electrons that emerge from the wall and accumulate on the exit side of the wall in an electron cloud.

2. The system according to claim 1, wherein the wall is manufactured from a conducting material.

3. The system according to claim 1, wherein the lens body is formed as an extended hollow body that is symmetrical with reference to its axis, whose end faces have openings, wherein the openings are arranged to be coaxial with the axis of symmetry.

4. The system according to claim 1, wherein the source for electromagnetic radiation is a pulsed laser whose laser beam has a power surface density of more than $10^{18}$ W/cm$^2$, and a pulse duration of less than several picoseconds.

5. The system according to claim 1, comprising a proton source for a laser-induced proton beam in a thin foil, which is arranged in the propagation direction of the beam in front of the lens.

6. The system according to claim 5, wherein the laser beam used for the proton source and the laser beam impinging onto the lens body are parts of the beam of a single laser.

7. The system according to claim 6, wherein the laser beam impinging onto the lens body can be delayed in time relative to the laser beam used for the proton source.

8. The system according to claim 1, wherein the wall of the lens body is manufactured from a metal foil of less than 100 μm.

9. The system according to claim 8, wherein the side wall is completely closed.

10. A method for the focusing of an ion beam by means of a lens placed into the beam path, wherein the lens has a lens body that surrounds an opening that is permeable to the ion beam, wherein within the lens body an electrostatic field is generated, which focuses the ion beam penetrating through the opening, and wherein the field is generated by external impingement of the thin walled lens body with electromagnetic radiation of high energy density.

11. The method according to claim 10, wherein the electrostatic field is generated with a pulsed laser beam.

12. The method according to claim 10, wherein via the level of insulation of the lens body a selectivity in the focusing for ions of a particular energy is generated.

13. A method for the focusing and/or collimation of a beam of high-energy protons, which are generated by means of laser pulses directed onto a thin foil comprising employing a system of claim 1.

14. A system of claim 1 wherein said beam is a beam of high energy protons.

15. A system of claim 2 wherein said conducting material is a thin metal foil.

16. A system of claim 4 wherein said density is $10^{19}$ W/cm$^2$.

17. A system of claim 7 wherein the delay is adjustable.

18. A system of claim 8 wherein the foil is less than 50 μm.

* * * * *